US008032873B2

(12) United States Patent
O'Brien et al.

(10) Patent No.: US 8,032,873 B2
(45) Date of Patent: *Oct. 4, 2011

(54) COMPUTER PROGRAM CODE SIZE PARTITIONING SYSTEM FOR MULTIPLE MEMORY MULTI-PROCESSING SYSTEMS

(75) Inventors: Kathryn M. O'Brien, South Salem, NY (US); John Kevin Patrick O'Brien, South Salem, NY (US)

(73) Assignee: International Business Machines Corporation, Armonk, NY (US)

( * ) Notice: Subject to any disclaimer, the term of this patent is extended or adjusted under 35 U.S.C. 154(b) by 470 days.

This patent is subject to a terminal disclaimer.

(21) Appl. No.: 12/337,197

(22) Filed: Dec. 17, 2008

(65) Prior Publication Data

US 2009/0158019 A1 Jun. 18, 2009

Related U.S. Application Data

(63) Continuation of application No. 11/002,552, filed on Dec. 2, 2004, now Pat. No. 7,478,376.

(51) Int. Cl.
*G06F 9/45* (2006.01)
*G06F 9/46* (2006.01)

(52) U.S. Cl. ............... 717/149; 717/159; 718/106

(58) Field of Classification Search .................. None
See application file for complete search history.

(56) References Cited

U.S. PATENT DOCUMENTS

| 4,991,088 A | 2/1991 | Kam |
| 5,021,945 A | 6/1991 | Morrison et al. |
| 5,787,284 A | 7/1998 | Blainey et al. |
| 5,889,999 A | 3/1999 | Breternitz, Jr. et al. |
| 6,760,906 B1 | 7/2004 | Odani et al. |
| 7,103,881 B2 | 9/2006 | Stone |
| 2006/0123382 A1 | 6/2006 | O'Brien et al. |

OTHER PUBLICATIONS

U.S. Appl. No. 11/002,550, Image File Wrapper printed May 17, 2011, 2 pages.
U.S. Appl. No. 11/002,552, Image File Wrapper printed May 17, 2011, 2 pages.
U.S. Appl. No. 12/350,458, Image File Wrapper printed May 17, 2011, 1 page.
Cheng, Wei-Kai et al., "Code Generation of Nested Loops for DSP Processors with Heterogeneous Registers and Structural Pipelining", ACM Transactions on Design Automation of Electronic Systems, vol. 4, No. 3, Jul. 1999, pp. 231-256.

(Continued)

*Primary Examiner* — James D Rutten
(74) *Attorney, Agent, or Firm* — Francis Lammes; Stephen J. Walder, Jr.; Matthew B. Talpis

(57) ABSTRACT

The present invention provides for a system for computer program code size partitioning for multiple memory multi-processor systems. At least one system parameter of a computer system comprising one or more disparate processing nodes is identified. Computer program code comprising a program to be run on the computer system is received. A program representation based on received computer program code is generated. At least one single-entry-single-exit (SESE) region is identified based on the whole program representation. At least one SESE region of less than a certain size (store-size-specific) is identified based on identified SESE regions and the at least one system parameter. Each store-size-specific SESE region is grouped into a node-specific subroutine. The non node-specific parts of the computer program code are modified based on the partitioning into node-specific subroutines. The modified computer program code including each node-specific subroutine is compiled based on a specified node characteristic.

13 Claims, 2 Drawing Sheets

OTHER PUBLICATIONS

Pino, Jose L. et al., "Mapping Multiple Independent Synchronous Dataflow Graphs onto Heterogeneous Multiprocessors", Signals, Systems and Computers, 1994 Conference Record of the Twenty-Eighth Asilomar Conference, vol. 2, Oct.-Nov. 1994, pp. 1063-1068.

Raulet, M. et al., "Automatic Coarse-Grain Partitioning and Automatic Code Generation for Heterogeneous Architectures", Signal Processing Systems, SIPS, IEEE Workshop, Aug. 2003, pp. 316-321.

Robson, J. M., "An Estimate of the Store Size Necessary for Dynamic Storage Allocation", J. ACM, DOI=http://doi.acm.org/10.1145/321650.321658, vol. 18, No. 3, Jul. 1971, pp. 416-423.

COMPUTER PROGRAM CODE SIZE PARTITIONING SYSTEM FOR MULTIPLE MEMORY MULTI-PROCESSING SYSTEMS

This application is a continuation of application Ser. No. 11/002,552, filed Dec. 2, 2004, status awaiting publication.

CROSS-REFERENCED APPLICATIONS

This application relates to co-pending U.S. patent application entitled COMPUTER PROGRAM FUNCTIONAL PARTITIONING SYSTEM AND METHOD FOR HETEROGENEOUS MULTI-PROCESSING SYSTEMS Ser. No. 11/002,550, filed concurrently herewith.

TECHNICAL FIELD

The present invention relates generally to the field of computer program development and, more particularly, to a system and method for computer program code size partitioning for multiple memory multi-processing systems.

BACKGROUND

Modern computer systems often employ complex architectures that can include a variety of processing units, with varying configurations and capabilities. In a common configuration, all of the processing units are identical, or homogeneous. Less commonly, two or more non-identical or heterogeneous processing units can be used, with differing local memory storage. In this case, the differing processors will have associated local memory storage, which is employed to store data and code executing within the processing unit. Each processor can be configured with differing local memory storage and, extremely, some processors can be inherently unable to execute entire programs that are too large to fit in the local memory storage. In this case, those programs must be split into smaller pieces that fit within the processor's local memory storage. Currently, partitioning large programs into pieces that fit in the target processor's local memory storage is done by the programmer, which is a major usability issue that can increase the time and complexity of the programming task.

The utility of a computer system is achieved by the process of executing specially designed software, herein referred to as computer programs or codes, on the processing unit(s) of the system. These codes are typically produced by a programmer writing in a computer language and are prepared for execution on the computer system by the use of a compiler. The ease of the programming task, and the efficiency of the ultimate execution of the code on the computer system are greatly affected by the facilities offered by the compiler. Many modern simple compilers produce slowly executing code for a single processor. Other compilers have been constructed that produce relatively extremely rapidly executing code for one or more processors in a homogeneous multi-processing system.

In general, for preparing programs for execution on heterogeneous multi-processing systems with varying or otherwise limited local memory, typical modern systems require a programmer to use several compilers and laboriously combine the results of these efforts to construct the final code. To do this, the programmer must partition the source program in such a way that the appropriate program segment sizes are sent to the appropriate processors used to execute the program code. In particular, where certain processors in the system are not capable of storing the entirety of executing program code, the partitioned program must fit within the local memory storage of the processor that is to execute the program code. Furthermore, even where multiple processor types are designed to perform the same function and are configured with similar local memory storage, to maximize the performance of the system, the partitioning should assign those functions to the processors that are most expeditious in the performance of said function while orchestrating the movement of the partitioned program pieces into local storage as needed without unreasonable performance degradation.

Therefore, there is a need for a system and/or method for computer program code size partitioning for multiple memory multi-processing systems that addresses at least some of the problems and disadvantages associated with conventional systems and methods.

SUMMARY OF THE INVENTION

The present invention provides for a method for computer program code size partitioning for multiple memory multi-processor systems. At least one system parameter of a computer system comprising one or more disparate processing nodes is identified. Computer program code comprising a program to be run on the computer system is received. A program representation based on received computer program code is generated. At least one single-entry-single-exit (SESE) region is identified based on the whole program representation. At least one SESE region of less than a certain size (store-size-specific) is identified based on identified SESE regions and the at least one system parameter. Each store-size-specific SESE region is grouped into a node-specific subroutine. The non node-specific parts of the computer program code are modified based on the partitioning into node-specific subroutines. The modified computer program code including each node-specific subroutine is compiled based on a specified node characteristic.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail. Additionally, for the most part, details concerning network communications, electromagnetic signaling techniques, user interface or input/output techniques, and the like, have been omitted inasmuch as such details are not considered necessary to obtain a complete understanding of the present invention, and are considered to be within the understanding of persons of ordinary skill in the relevant art.

It is further noted that, unless indicated otherwise, all functions described herein may be performed in either hardware or software, or in some combinations thereof. In a preferred embodiment, however, the functions are performed by a processor such as a computer or an electronic data processor in accordance with code such as computer program code, software, and/or integrated circuits that are coded to perform such functions, unless indicated otherwise.

Figure 1:
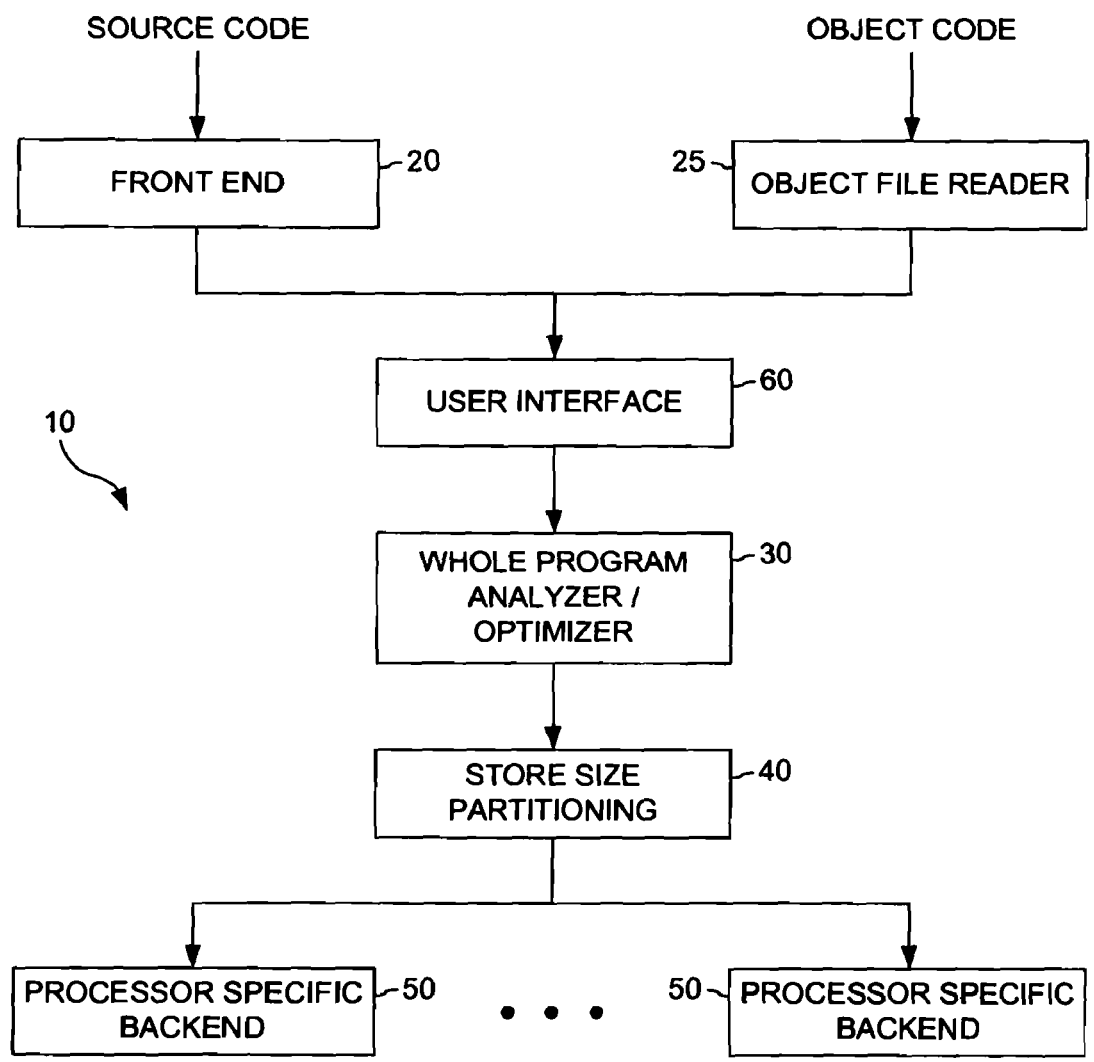
FIG. 1 is a block diagram depicting a computer program code size partitioning system.

Referring to FIG. 1 of the drawings, the reference numeral 10 generally designates a compiler. Compiler 10 is a circuit or circuits or other suitable logic and is configured as a computer program code compiler. In a particular embodiment, compiler 10 is a software program configured to compile source code into object code, as described in more detail below. Generally, compiler 10 is configured to receive source code in front end code module 20, through user interface 60, and to receive object code through object file reader 25. The received code is then processed using parameters provided by whole program analyzer and optimizer 30 and store size partitioning module 40, to generate store-size specific back end code 50, as described in more detail below.

In particular, in the illustrated embodiment, compiler 10 includes user interface 60. User interface 60 is a circuit or circuits or other suitable logic and is configured to receive input from a user. In one embodiment, user interface 60 is a combination of inserted "pragmas" commands or directives in the program source code and compiler option flags provided on a command line, or in a "makefile" command or script. In another embodiment a graphical user interface can be employed to provide this information. It will be understood to one skilled in the art that other configurations can also be employed.

Compiler 10 includes front end code module 20. Front end code module 20 is a circuit or circuits or other suitable logic and is configured to read source code and to identify particular parameters of the computer system on which compiled code is to be executed. Compiler 10 also includes object file reader module 25. Object file reader module 25 is a circuit or circuits or other suitable logic and is configured to read object code and to identify particular parameters of the computer system on which compiled code is to be executed. Generally, object code is the saved result of previously processing source code received by front end code module 20 through compiler 10 and storing information about said source code derived by analysis in the compiler. In a particular embodiment, object file reader module 25 is a software program and is configured to identify and map the various local memory storage capacities of the processing nodes of the computer system on which compiled code is to be executed, the "target" system. Additionally, object file reader module 25 can also be configured to identify the processing capabilities of identified nodes.

Compiler 10 also includes whole program analyzer and optimizer module 30. Whole program analyzer and optimizer module 30 is a circuit or circuits or other suitable logic and is configured to analyze received source and/or object code as described in more detail below. In a particular embodiment, whole program analyzer and optimizer module 30 is a software program and is configured to create a whole program representation of received source and/or object code, and to identify store-size-specific segments of computer program code. Thus, generally, whole program analyzer and optimizer module 30 can be configured to analyze an entire computer program, that is, received source and/or object code, to identify segments of said computer code that fit within the local memory storage of the target processing node, and to isolate identified segments into subroutines that can be subsequently compiled for the particular required processing node, the "target" node. As used herein, an entire computer program source code is a set of lines of computer program code that make up a discrete computer program, as will be understood to one skilled in the art.

In particular, in one embodiment, whole program analyzer and optimizer module 30 is configured to receive source and/or object code and to create a whole program representation of received code. As used herein, a whole program representation is a representation of the various code segments that make up an entire computer program source code. In one embodiment, whole program analyzer and optimizer module 30 is configured to perform Inter-Procedural Analysis on the received source and/or object code to create a whole program representation. It will be understood to one skilled in the art that other methods can also be employed to create a whole program representation of the received computer program source code.

In one embodiment, whole program analyzer and optimizer module 30 is also configured to identify Single-Entry-Single-Exit (SESE) regions within the whole program representation. Generally, SESE regions are segments within a computer program that adhere to certain well-known characteristics with respect to the process flow of the computer program as a whole, as will be understood to one skilled in the art. Thus, identified SESE regions can be employed to facilitate partitioning the program into subroutines. It will be understood to one skilled in the art that other suitable program fragments that are not strictly defined SESE regions can be converted to SESE regions through appropriate transformations. In a particular embodiment, whole program analyzer and optimizer module 30 is configured to identify SESE regions through construction and analysis of a Program Structure Tree. It will be understood to one skilled in the art that other methods can also be employed to identify SESE regions within the whole program representation.

Additionally, whole program analyzer and optimizer module 30 can be configured to identify SESE regions that meet the local memory storage size capacity for the destination processing node. In particular, whole program analyzer and optimizer module 30 can be configured to receive system parameters and/or system parameters information from object file reader 25 and/or user interface 60, to identify SESE regions that meet the local memory storage size capacity for the destination processing node, and to correlate the identified SESE regions with the capabilities of the particular computer system nodes as described by the system parameters. It will be understood to one skilled in the art that the local memory storage size capacity for the destination processing node can include a buffer or other reserved capacity to account for the maximum local memory storage size capacity, less a suitable allowance for data storage. Thus, generally, in one embodiment, whole program analyzer and optimizer module 30 is configured to identify store-size-specific SESE regions, based on the system parameters of the target system and, more particularly, the target node.

Additionally, whole program analyzer and optimizer module 30 can be configured to identify SESE regions proximate to identified store-size-specific SESE regions in the overall process flow. Thus, whole program analyzer and optimizer module 30 can be further configured to identify proximate SESE regions that can be grouped with identified store-size-specific SESE regions based on system efficiency for the target computer system. Thus, whole program analyzer and optimizer module 30 can be configured to provide for increased process efficiency through grouping identified proximate SESE regions with identified store-size-specific SESE regions. It will be understood to one skilled in the art that grouping identified proximate SESE regions with identified store-size-specific SESE regions can be based on the ability of the particular processing node to process the identified proximate SESE regions, including both functional capability and local memory storage capacity.

Compiler 10 also includes store size partitioning module 40. Store size partitioning module 40 is a circuit or circuits or other suitable logic and is configured, generally, to partition identified store-size-specific SESE regions into subroutines and to compile the subroutines for the target node on which the particular subroutine is to execute. Thus, in a particular embodiment, store size partitioning module 40 is configured to group identified store-size-specific SESE regions into discrete subroutines. In one embodiment, store size partitioning module 40 can be configured to group each identified store-size-specific SESE region into a separate subroutine. In an alternate embodiment, store size partitioning module 40 can also be configured to group one or more identified store-size-specific SESE regions into a composite subroutine. It will be understood to one skilled in the art that grouping one or more identified store-size-specific SESE regions into a composite subroutine can be subject to programming suitability for grouping said regions. For example, one or more identified store-size-specific SESE regions can be unsuitable for grouping into a composite subroutine when the regions are located at points in the overall process flow that require incompatible intermediate process steps, as will be understood to one skilled in the art.

Additionally, store size partitioning module 40 can also be configured to group identified store-size-specific SESE regions and/or identified proximate SESE regions based on input received from a user through user interface 60. Thus, for example, in one embodiment, compiler 10 can be configured to present identified store-size-specific SESE regions and/or identified proximate SESE regions to a user, through user interface 60, and to group presented regions based on user input.

In one embodiment, store size partitioning module 40 is also configured to modify received source and/or object code based on grouped subroutines. In a particular embodiment, store size partitioning module 40 is configured to modify received source and/or object code through sequencing instructions. In particular, store size partitioning module 40 can be configured to insert timing overlays into the received source and/or object code, thereby orchestrating the execution timing for the subroutines. For example, inserting timing overlays can include pre-loading particular code segments to help ensure proper program functionality, to help minimize or eliminate delays in code execution, and for other suitable timing considerations. It will be understood to one skilled in the art that other configurations can also be employed.

Store size partitioning module 40 is also configured to compile received source and/or object code into one or more processor specific backend code segments 50, as appropriate, based on the particular processing node on which the compiled processor specific backend code segments 50 is to execute, that is, the target node. Thus, the processor specific backend code segments 50 are compiled for the node-specific functionality required to support the particular functions embodied within the code segments as well as the local memory store capacity.

Therefore, generally, in operation, compiler 10 receives computer program code (source and/or object code) and analyzes received computer program code for store-size-specific SESE regions based on the target system parameters. Store-size-specific SESE regions are grouped into subroutines and compiled for their target node, along with appropriate proximate SESE regions, if any. Accordingly, compiler 10 can be configured to automate certain time-intensive programming activities, such as identifying store-size-specific SESE regions and grouping identified store-size-specific SESE regions into subroutines, thereby shifting the burden from the human programmer who would otherwise have to perform the tasks. Thus, compiler 10 can be configured to partition computer program code into store-size-specific subroutines, compiled for a particular type of target node on which they will execute, with sequencing instructions to maintain process timing and control.

Figure 2:
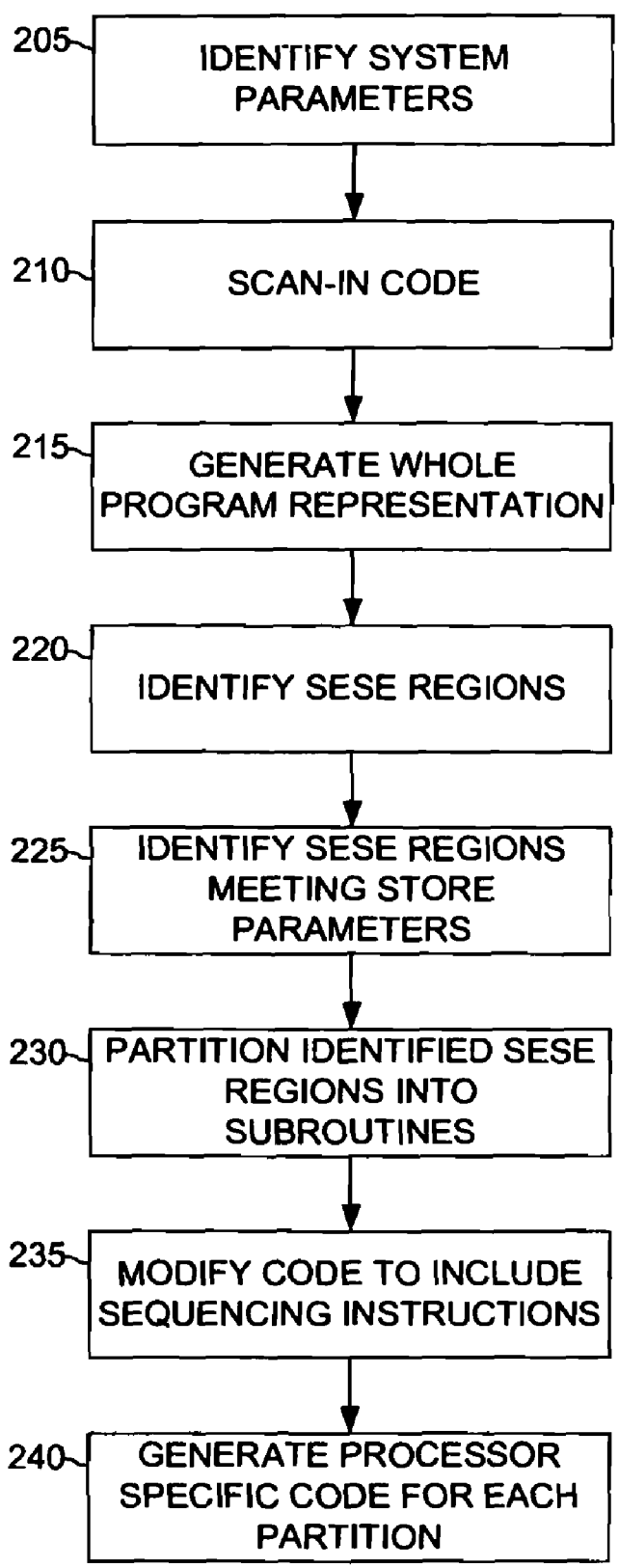
FIG. 2 is a flow diagram depicting a computer program code size partitioning method.

Referring to FIG. 2 of the drawings, the reference numeral 200 generally designates a flow chart depicting a computer program partitioning method. The process begins at step 205, wherein system parameters are identified. This step can be performed by, for example, object file reader module 25 of FIG. 1 and/or through user input received through user interface 60 of FIG. 1. At next step 210, computer program code to be analyzed is received or scanned in. This step can be performed by, for example, a compiler front end and/or front end code module 20 or object file reader module 25 of FIG. 1. It will be understood to one skilled in the art that receiving or scanning in code to be analyzed can include retrieving data stored on a hard drive or other suitable storage device and loading the data into a system memory. Additionally, in the case of the compiler front end and/or front end code module 20, this step can also include parsing a source language program and producing an intermediate form code. In the case of object file reader module 25, this step can include extracting an intermediate representation from an object code file of the computer program code.

At next step 215, a whole program representation is generated based on received computer program code. This step can be performed by, for example, whole program analyzer and optimizer module 30 of FIG. 1. This step can include conducting Inter Procedural Analysis, as will be understood to one skilled in the art. At next step 220, SESE regions are identified based on the whole program representation. This step can be performed by, for example, whole program analyzer and optimizer module 30 of FIG. 1. This step can include generating a Program Structure Tree, as will be understood to one skilled in the art.

At next step 225, store-size-specific SESE regions are identified based on identified system parameters and identified SESE regions. This step can be performed by, for example, whole program analyzer and optimizer module 30 of FIG. 1. This step can also include identifying proximate SESE regions suitable to be grouped with identified store-size-specific SESE regions, as described above. At next step 230, identified store-size-specific SESE regions are grouped into one or more store-size-specific subroutines or partitions. This step can be performed by, for example, store size partitioning module 40 of FIG. 1. This step can include grouping each store-size-specific SESE region into its own subroutine or partition and/or grouping one or more store-size-specific SESE regions into a composite subroutine or partition, as described above.

At next step 235, the received computer program code is modified to include sequencing instructions for the one or more subroutines. This step can be performed by, for example, store size partitioning module 40 of FIG. 1. This step can include instructions to transfer code and/or data between processors as required, and instructions to check for completion of partitions executing on other processors and to perform other appropriate actions, as will be understood to one skilled in the art.

At next step 240, processor specific code is generated for each partition and the process ends. This step can be performed by, for example, store size partitioning module 40 of FIG. 1. Thus, a computer program can be partitioned into subroutines that are marked for compilation to a particular node type, with sequencing modifications to orchestrate communication between various node types in the target system. Accordingly, computer program code designed for a multi-processor system with disparate or heterogeneous processing elements with differing or limited local memory storage can be configured to account for local memory storage capacity restrictions, as well as certain functions that are required to be executed on a particular type of node.

Thus, the present invention provides for computer program code size partitioning among the nodes of a heterogeneous multiple memory multi-processor system, with at least two disparate processors. The compiler is configured to generate code specific to each of the disparate processors that meets the processors' local memory storage capacities. Generally, the compiler reads the source program, which may be distributed into many files and may be processed at different times, and builds a model, or representation, of the whole program. This model is then analyzed according to the characteristics of the multiple disparate processors, or nodes. One or more program segments are identified within the model that meet the local memory storage capacity, or otherwise are better suited to execution on particular processor types. A single-entry-single-exit region (SESE) wholly enclosing the identified program segments is identified, in such a way as to optimize the overall execution time of the program, which is extracted into a store-size-specific subroutine. The extracted SESE region is replaced with appropriate linkage or sequencing code to ensure correct and efficient program execution. Each of the resulting processor specific partitions or subroutines are compiled for their respective processors and the resultant compilations are integrated, to form the final program for execution on the heterogeneous multiple memory multi-processor system.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A computer program product for computer program code size partitioning for multiple memory multi-processor systems, the computer program product having a medium with a computer program embodied thereon, the computer program, when executed on a computing device, causes the computing device to:
    identify at least one system parameter of a computer system comprising one or more disparate processing nodes;
    receive computer program code comprising a program to be run on the computer system;
    generate a program representation based on received computer program code;
    identify at least one single-entry-single-exit (SESE) region based on the program representation;
    identify at least one store-size-specific SESE region based on identified SESE regions and the at least one system parameter, thereby forming a specified node;
    identify SESE regions proximate to the identified store-size-specific SESE region based on an ability of the specified node to process the identified proximate SESE regions, wherein the identified proximate SESE regions are grouped with the identified store-size-specific SESE regions and are configured to be compiled for the specified node;
    present the identified store-size-specific SESE regions and the identified proximate SESE regions to a user;
    receive user input from the user as to a grouping that should be used for the identified store-size-specific SESE regions and the identified proximate SESE regions;
    group each store-size-specific SESE region with at least one proximate SESE region into a node-specific subroutine based on the user input;
    modify the computer program code based on the node-specific subroutines; and
    compile the modified computer program code including each node-specific subroutine based on a specified node characteristic.

2. The computer program product as recited in claim 1, wherein the at least one system parameter comprises a local memory storage capacity.

3. The computer program code as recited in claim 1, wherein the computer program to generate the program representation further causes the computing device to:
    perform an Inter Procedural Analysis of the whole program.

4. The computer program code as recited in claim 1, wherein the computer system comprises a Broadband Processor Architecture system.

5. The computer program code as recited in claim 1, wherein the computer program further causes the computing device to:
    generate a program structure tree.

6. The computer program code as recited in claim 1, wherein the computer program to modify the computer program code further causes the computing device to:
    generate sequencing instructions.

7. The computer program code as recited in claim 1, wherein the computer program further causes the computing device to:
    receive input from a user; and
    identify the at least one system parameter of the computer system based on the input.

8. A compiler, comprising:
    an object file reader module configured to identify at least one system parameter of a computer system comprising one or more disparate processing nodes;
    a whole program analyzer and optimizer module coupled to the object file reader module and configured:
        to receive computer program code comprising a program to be run on the computer system,
        to generate a program representation based on received computer program code,
        to identify at least one single-entry-single-exit (SESE) region based on the program representation,
        to identify at least one store-size-specific SESE region based on identified SESE regions and the at least one system parameter, thereby forming a specified node,
        to identify SESE regions Proximate to the identified store-size-specific SESE region based on an ability of the specified node to process the identified proximate SESE regions, wherein the identified proximate SESE regions are grouped with the identified store-size-specific SESE regions and are configured to be compiled for the specified node, to present the identified store-size-specific SESE regions and the identified proximate SESE regions to a user, and to receive user input from the user as to a grouping that should be used for the identified store-size-specific SESE regions and the identified proximate SESE regions, and a store size partitioning module coupled to the whole program analyzer and optimizer module and configured:

to group each store-size-specific SESE region with at least one proximate SESE region into a node-specific subroutine based on the user input, to modify the computer program code based on the node-specific subroutines, and to compile the modified computer program code including each node-specific subroutine based on a specified node characteristic, wherein the object file reader module, the whole program analyzer and optimizer module, and the store size partitioning module are stored on a computer readable storage medium for execution by a processor.

9. The compiler as recited in claim 8, wherein generating a the program representation comprises an Inter Procedural Analysis.

10. The compiler as recited in claim 8, wherein the computer system comprises a Broadband Processor Architecture system.

11. The compiler as recited in claim 8, wherein the whole program analyzer and the optimizer module is further configured to generate a program structure tree.

12. The compiler as recited in claim 8, wherein modifying the computer program code comprises generating sequencing instructions.

13. The compiler as recited in claim 8, further comprising:
a user interface configured to receive input from a user; and
wherein the whole program analyzer and optimizer module is further configured to identify the at least one system parameter of the computer system based on the input.

\* \* \* \* \*